United States Patent
Faulks

(10) Patent No.: US 7,086,095 B2
(45) Date of Patent: Aug. 8, 2006

(54) BOXER-STYLE ABSORBENT UNDERPANT AND METHOD OF MAKING SAME

(75) Inventor: Michael J. Faulks, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 186 days.

(21) Appl. No.: 10/301,086

(22) Filed: Nov. 21, 2002

(65) Prior Publication Data

US 2004/0098791 A1    May 27, 2004

(51) Int. Cl.
*A41B 9/00* (2006.01)
(52) U.S. Cl. ............................................. 2/400; 2/403
(58) Field of Classification Search ............ 2/400–408, 2/228, 238; 604/385.01–402
See application file for complete search history.

(56) References Cited

U.S. PATENT DOCUMENTS

| | | |
|---|---|---|
| 478,281 A | 7/1892 | Hamilton et al. |
| 1,577,409 A | 3/1926 | Rand |
| 1,664,298 A | 3/1928 | Katz |
| 1,971,558 A | 8/1934 | Goodman |
| 2,030,306 A | 2/1936 | Lain |
| 2,032,982 A | 3/1936 | Gerstman |
| 2,088,302 A | 7/1937 | McKeever |
| 2,116,822 A | 5/1938 | Berger |
| 2,242,526 A | 5/1941 | Kneibler |
| 2,252,019 A | 8/1941 | Meinecke et al. |
| 2,319,138 A | 5/1943 | Kneibler |
| 2,391,641 A | 12/1945 | O'Hern |
| 2,435,945 A | 2/1948 | Redmond |
| 2,450,789 A | 10/1948 | Frieman |
| 2,522,510 A | 9/1950 | Fridolph |
| 2,538,596 A | 1/1951 | Sheridan |
| 2,675,806 A | 1/1954 | Bram |
| 2,711,735 A | 6/1955 | Sabo |
| 2,838,047 A | 6/1958 | Sidnell |
| 2,842,129 A | 7/1958 | Emstorff |
| 2,859,752 A | 11/1958 | Haber |
| 3,245,407 A | 4/1966 | Mason |

(Continued)

FOREIGN PATENT DOCUMENTS

AT        168478        6/1951

(Continued)

OTHER PUBLICATIONS

Printed materials (3 pages) showing pull-on diapers disclosed at a trade show Apr. 27-29, 2004 in Miami Beach, Florida, U.S.A.

(Continued)

*Primary Examiner*—Gloria M. Hale
(74) *Attorney, Agent, or Firm*—Pauley Petersen & Erickson

(57) ABSTRACT

A method of making a pant having side seams and side-to-side crotch seams from a flat web. The method can be carried out in either the cross-machine direction or in the machine direction. The method includes providing a z-slit in selected areas along the flat web and folding the resulting flaps back onto the flat web. In the cross-machine direction process, the flat web is folded, side seams and crotch seams are formed and individual pants are cut. In the machine direction process, the flat web is cut into individual garment shells, which are folded, and side seams and crotch seams are formed. In either the cross-machine process or the machine process, the method can also include attaching an absorbent structure to the flat web.

17 Claims, 11 Drawing Sheets

U.S. PATENT DOCUMENTS

| | | |
|---|---|---|
| 3,338,992 A | 8/1967 | Kinney |
| 3,341,394 A | 9/1967 | Kinney |
| 3,418,660 A | 12/1968 | Shumate |
| 3,502,538 A | 3/1970 | Petersen |
| 3,502,763 A | 3/1970 | Hartmann |
| 3,542,615 A | 11/1970 | Dobo et al. |
| 3,611,443 A | 10/1971 | Braun |
| 3,648,699 A | 3/1972 | Anderson et al. |
| 3,678,516 A * | 7/1972 | Backer .......................... 2/402 |
| 3,692,618 A | 9/1972 | Dorschner et al. |
| 3,714,946 A | 2/1973 | Rudes |
| 3,739,398 A * | 6/1973 | Sarmiento ...................... 2/407 |
| 3,802,817 A | 4/1974 | Matsuki et al. |
| 3,806,007 A | 4/1974 | Grantham |
| 3,844,282 A | 10/1974 | King |
| 3,859,667 A | 1/1975 | Roy |
| 3,869,999 A | 3/1975 | Richter |
| 3,920,237 A | 11/1975 | Grantham |
| 4,059,257 A | 11/1977 | Grantham |
| 4,081,301 A | 3/1978 | Buell |
| 4,100,324 A | 7/1978 | Anderson et al. |
| 4,114,621 A | 9/1978 | Mims, Jr. |
| 4,145,763 A | 3/1979 | Abrams et al. |
| 4,227,952 A | 10/1980 | Sabee |
| 4,280,230 A | 7/1981 | LaFleur |
| 4,284,454 A | 8/1981 | Joa |
| 4,300,241 A | 11/1981 | Shaull |
| 4,310,929 A * | 1/1982 | Finlay .......................... 2/238 |
| 4,327,448 A * | 5/1982 | Lunt ............................ 2/404 |
| 4,338,939 A | 7/1982 | Daville |
| 4,340,563 A | 7/1982 | Appel et al. |
| 4,368,565 A | 1/1983 | Schwarz |
| 4,392,259 A | 7/1983 | Bredo |
| 4,397,704 A | 8/1983 | Frick |
| 4,417,938 A | 11/1983 | Sigl |
| 4,449,254 A | 5/1984 | Fogg |
| 4,555,245 A | 11/1985 | Armbruster |
| 4,597,110 A | 7/1986 | Smith, Sr. et al. |
| 4,608,115 A | 8/1986 | Schroth et al. |
| 4,644,945 A | 2/1987 | Thorner |
| 4,646,362 A * | 3/1987 | Heran et al. ................... 2/400 |
| 4,650,530 A | 3/1987 | Mahoney et al. |
| 4,655,760 A | 4/1987 | Morman et al. |
| 4,663,106 A | 5/1987 | Pomplun et al. |
| 4,663,220 A | 5/1987 | Wisneski et al. |
| 4,665,306 A | 5/1987 | Roland et al. |
| 4,671,793 A | 6/1987 | Hults et al. |
| 4,675,918 A | 6/1987 | O'Brien |
| 4,704,116 A | 11/1987 | Enloe |
| 4,745,636 A | 5/1988 | Lunt |
| 4,748,636 A * | 5/1988 | Kato .......................... 375/141 |
| 4,771,483 A | 9/1988 | Hooreman et al. |
| 4,786,346 A | 11/1988 | Ales et al. |
| 4,805,243 A | 2/1989 | Gibbens et al. |
| 4,816,094 A | 3/1989 | Pomplun et al. |
| 4,835,795 A | 6/1989 | Lonon |
| 4,847,134 A | 7/1989 | Fahrenkrug et al. |
| 4,870,958 A | 10/1989 | Webster |
| 4,872,221 A | 10/1989 | Stone, III |
| 4,875,240 A | 10/1989 | Barrett |
| 4,883,549 A | 11/1989 | Frost et al. |
| 4,892,536 A | 1/1990 | DesMarais et al. |
| 4,895,568 A | 1/1990 | Enloe |
| 4,935,021 A | 6/1990 | Huffman et al. |
| 4,946,539 A | 8/1990 | Ales et al. |
| 4,955,880 A | 9/1990 | Rodriquez |
| 4,964,860 A | 10/1990 | Gipson et al. |
| D315,050 S | 3/1991 | Bush et al. |
| 5,014,364 A | 5/1991 | Orr |
| 5,022,240 A | 6/1991 | Peleg |
| 5,046,272 A | 9/1991 | Vogt et al. |
| 5,052,058 A | 10/1991 | Mueller |
| 5,067,178 A | 11/1991 | Katchka |
| 5,087,253 A | 2/1992 | Cooper |
| 5,103,505 A | 4/1992 | Llorens |
| 5,135,522 A | 8/1992 | Fahrenkrug et al. |
| 5,171,388 A | 12/1992 | Hoffman et al. |
| 5,187,817 A | 2/1993 | Zolner |
| 5,210,882 A | 5/1993 | Moretz et al. |
| 5,217,782 A | 6/1993 | Moretz et al. |
| 5,226,992 A | 7/1993 | Morman |
| D341,243 S | 11/1993 | Costella et al. |
| 5,297,296 A | 3/1994 | Moretz et al. |
| 5,303,424 A | 4/1994 | Cromartie |
| 5,306,536 A | 4/1994 | Moretz et al. |
| 5,315,716 A | 5/1994 | Baum |
| 5,315,717 A | 5/1994 | Moretz et al. |
| 5,370,634 A | 12/1994 | Ando et al. |
| 5,379,462 A | 1/1995 | Morgan et al. |
| 5,382,246 A | 1/1995 | Kawano |
| 5,435,014 A | 7/1995 | Moretz et al. |
| 5,445,628 A | 8/1995 | Gipson et al. |
| 5,500,063 A | 3/1996 | Jessup |
| 5,545,158 A | 8/1996 | Jessup |
| 5,549,593 A | 8/1996 | Ygge et al. |
| 5,556,504 A | 9/1996 | Rajala et al. |
| 5,566,392 A | 10/1996 | Dzelzkalns |
| D377,557 S | 1/1997 | Jagger |
| 5,649,913 A | 7/1997 | Cohen |
| D382,386 S | 8/1997 | Malone |
| 5,669,902 A | 9/1997 | Sivilich |
| 5,669,996 A | 9/1997 | Jessup |
| 5,690,626 A | 11/1997 | Suzuki et al. |
| 5,690,627 A | 11/1997 | Clear et al. |
| 5,716,478 A | 2/1998 | Boothe et al. |
| 5,718,003 A | 2/1998 | Gwinn |
| 5,733,401 A | 3/1998 | Linman et al. |
| 5,746,730 A | 5/1998 | Suzuki et al. |
| 5,755,902 A | 5/1998 | Reynolds |
| 5,759,340 A | 6/1998 | Boothe et al. |
| 5,790,983 A | 8/1998 | Rosch et al. |
| 5,827,260 A * | 10/1998 | Suzuki et al. .......... 604/385.24 |
| 5,853,405 A | 12/1998 | Suprise |
| 5,876,394 A | 3/1999 | Rosch et al. |
| 5,891,122 A | 4/1999 | Coates |
| D408,964 S | 5/1999 | Hernandez |
| 5,906,604 A | 5/1999 | Rönnberg et al. |
| 5,906,879 A | 5/1999 | Huntoon et al. |
| 5,907,872 A | 6/1999 | Alberts et al. |
| 5,921,974 A * | 7/1999 | Kikuchi ................. 604/385.24 |
| 5,953,754 A | 9/1999 | Rosch et al. |
| 5,956,774 A | 9/1999 | Mackley |
| 5,978,971 A | 11/1999 | Wald |
| D417,940 S | 12/1999 | Coates et al. |
| 6,009,558 A | 1/2000 | Rosch et al. |
| 6,010,586 A | 1/2000 | Suprise |
| 6,018,822 A | 2/2000 | Hernandez |
| 6,022,443 A | 2/2000 | Rajala et al. |
| 6,105,171 A | 8/2000 | Niedermeyer |
| 6,142,983 A | 11/2000 | Suprise et al. |
| 6,145,132 A | 11/2000 | Towner |
| 6,149,637 A | 11/2000 | Allen et al. |
| 6,149,755 A | 11/2000 | McNichols et al. |
| 6,168,585 B1 | 1/2001 | Cesco-Cancian |
| 6,174,303 B1 | 1/2001 | Suprise et al. |
| 6,192,521 B1 | 2/2001 | Alberts et al. |
| 6,205,592 B1 | 3/2001 | Gouws |
| 6,248,097 B1 | 6/2001 | Beitz et al. |
| 6,287,169 B1 | 9/2001 | Willms et al. |
| 6,289,519 B1 | 9/2001 | Murakami et al. |
| 6,293,934 B1 | 9/2001 | Kumasaka |
| 6,293,936 B1 | 9/2001 | Otsubo |
| 6,293,937 B1 | 9/2001 | Matsushita et al. |
| 6,308,339 B1 | 10/2001 | Murakami et al. |

| | | | |
|---|---|---|---|
| 6,312,420 B1 | 11/2001 | Sasaki et al. | |
| 6,319,347 B1 | 11/2001 | Rajala et al. | |
| 6,342,050 B1 | 1/2002 | Rönnberg et al. | |
| 6,368,312 B1 | 4/2002 | Otsubo | |
| D456,995 S | 5/2002 | Baker | |
| 6,463,591 B1 | 10/2002 | Toratani | |
| 6,475,201 B1 | 11/2002 | Saito et al. | |
| 6,516,473 B1 | 2/2003 | Saito | |
| 6,539,554 B1 | 4/2003 | Portela | |
| 6,560,786 B1 | 5/2003 | Lipton | |
| 6,585,840 B1 | 7/2003 | Rabe et al. | |
| 6,626,883 B1 | 9/2003 | Wada et al. | |
| 6,666,851 B1 | 12/2003 | Otsubo et al. | |
| 2001/0014798 A1 | 8/2001 | Femfors | |
| 2001/0044614 A1 | 11/2001 | Damay et al. | |
| 2002/0000291 A1 | 1/2002 | Coenen et al. | |
| 2002/0002021 A1 | 1/2002 | May et al. | |
| 2002/0002358 A1 | 1/2002 | Durrance et al. | |
| 2002/0009940 A1 | 1/2002 | May et al. | |
| 2002/0084017 A1 | 7/2002 | Rabe et al. | |
| 2002/0087137 A1 | 7/2002 | Christoffel et al. | |
| 2002/0099345 A1 | 7/2002 | Saito et al. | |
| 2003/0109842 A1 | 6/2003 | Louis et al. | |
| 2003/0115660 A1 | 6/2003 | Hopkins | |
| 2004/0102746 A1 | 5/2004 | Mortell et al. | |
| 2004/0107481 A1 | 6/2004 | Mortell et al. | |
| 2004/0116881 A1 | 6/2004 | Nordness et al. | |

FOREIGN PATENT DOCUMENTS

| | | |
|---|---|---|
| CA | 2 356 510 | 2/2003 |
| DE | 435 579 | 2/1927 |
| DE | 809 844 | 8/1951 |
| DE | 839 244 | 5/1952 |
| DE | 101 44 255 C1 | 2/2003 |
| EP | 217 032 | 4/1987 |
| EP | 0 717 971 | 6/1996 |
| EP | 763 353 | 3/1997 |
| EP | 549 988 | 6/1998 |
| EP | 904 758 | 3/1999 |
| EP | 911 006 | 4/1999 |
| EP | 0 925 729 A2 | 6/1999 |
| EP | 933 072 | 8/1999 |
| EP | 1 048 231 | 11/2000 |
| EP | 1 060 677 | 12/2000 |
| EP | 1 060 679 | 12/2000 |
| EP | 1 108 371 | 6/2001 |
| EP | 1 108 372 | 6/2001 |
| EP | 1 108 373 | 6/2001 |
| EP | 1 110 463 | 6/2001 |
| EP | 1 118 277 | 7/2001 |
| EP | 1 125 571 | 8/2001 |
| EP | 1 159 883 | 12/2001 |
| EP | 1 166 730 | 1/2002 |
| EP | 1 179 302 | 2/2002 |
| EP | 1 184 012 | 3/2002 |
| EP | 1 188 427 | 3/2002 |
| FR | 1.276.791 | 10/1960 |
| FR | 1.276.791 | 10/1961 |
| GB | 238557 | 8/1926 |
| GB | 307652 | 3/1929 |
| GB | 571098 | 8/1945 |
| GB | 620555 | 3/1949 |
| GB | 701081 | 12/1953 |
| GB | 1 342 022 | 12/1973 |
| GB | 2 069 820 A | 9/1981 |
| GB | 2 112 268 | 7/1983 |
| GB | 2 196 525 | 5/1988 |
| GB | 2 208 263 | 3/1989 |
| GB | 2 269 978 | 3/1994 |
| GB | 2 269 998 | 3/1994 |
| GB | 2 269 999 | 3/1994 |
| GB | 2 327 859 | 2/1999 |
| JP | 2000 355801 | 12/2000 |
| JP | 2001 172801 | 6/2001 |
| JP | 2001 172802 | 6/2001 |
| JP | 3177341 | 6/2001 |
| JP | 2001 204762 | 7/2001 |
| JP | 2001 204764 | 7/2001 |
| JP | 2001 204765 | 7/2001 |
| JP | 3182069 | 7/2001 |
| JP | 2001 207301 | 8/2001 |
| JP | 2001 224615 | 8/2001 |
| JP | 2001 238909 | 9/2001 |
| JP | 2001 245929 | 9/2001 |
| JP | 2001 248002 | 9/2001 |
| JP | 2001 254202 | 9/2001 |
| JP | 2001 262402 | 9/2001 |
| JP | 3205643 | 9/2001 |
| JP | 3205690 | 9/2001 |
| JP | 3208258 | 9/2001 |
| JP | 2001 299813 | 10/2001 |
| JP | 3221601 | 10/2001 |
| JP | 2001 309946 | 11/2001 |
| JP | 2001 333932 | 12/2001 |
| JP | 2002-320641 | 11/2002 |
| JP | 2004 159949 | 6/2004 |
| WO | 95/16421 | 6/1995 |
| WO | 95/18589 | 7/1995 |
| WO | 96/03950 | 2/1996 |
| WO | WO 97/02797 | 1/1997 |
| WO | 99/33421 | 7/1999 |
| WO | WO 01/03524 | 1/2001 |
| WO | 01/58401 | 8/2001 |
| WO | 01/61093 | 8/2001 |
| WO | 01/67900 | 9/2001 |
| WO | 01/87217 | 11/2001 |
| WO | 01/87218 | 11/2001 |
| WO | 01/87562 | 11/2001 |
| WO | 01/87753 | 11/2001 |
| WO | 01/88245 | 11/2001 |
| WO | 02/49565 | 6/2002 |
| WO | 02/52967 | 7/2002 |
| WO | WO 03/057107 A1 | 7/2003 |

OTHER PUBLICATIONS

US 5,915,536, 06/1999, Alberts et al. (withdrawn)

* cited by examiner

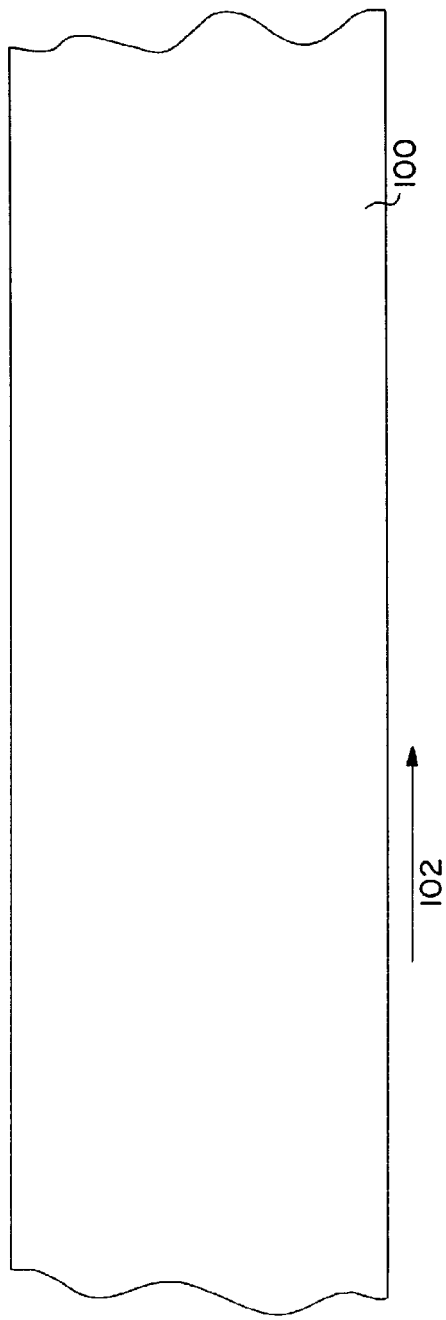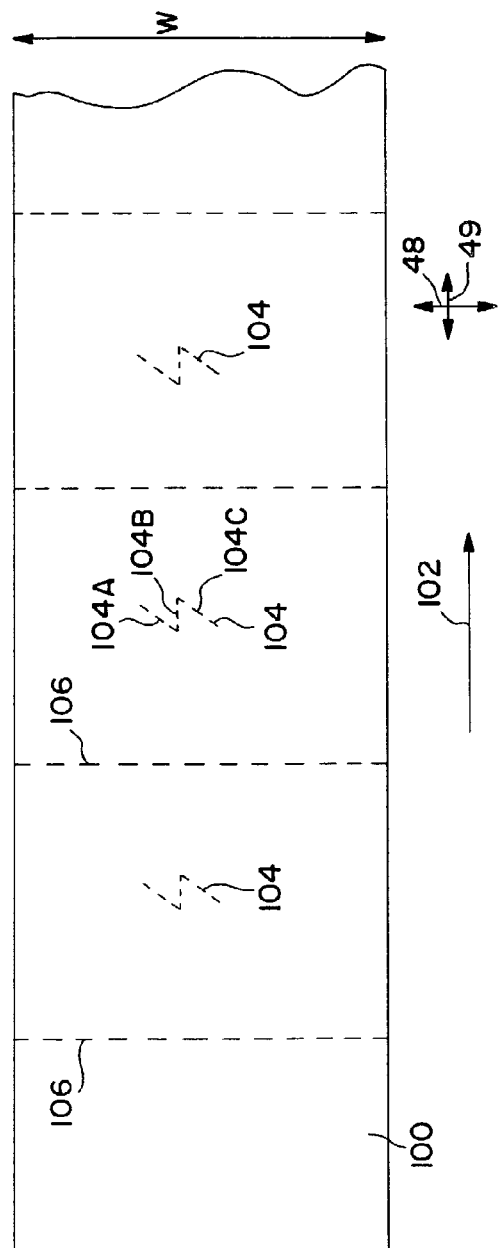

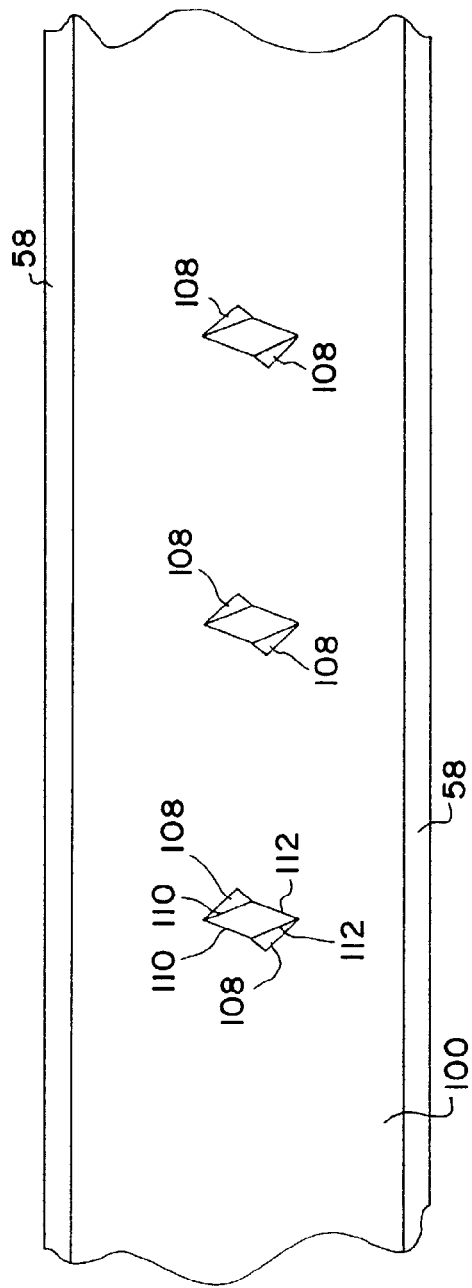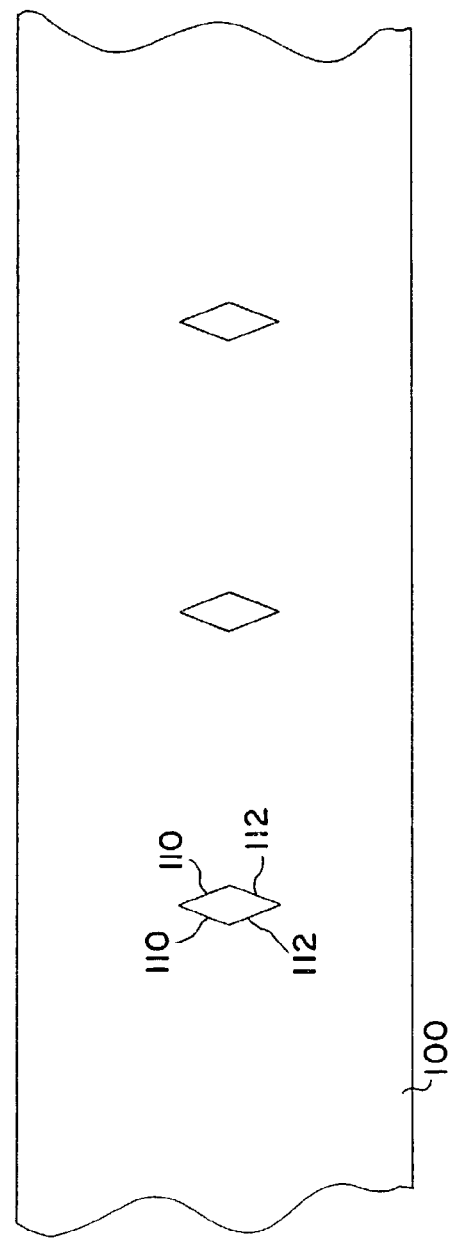

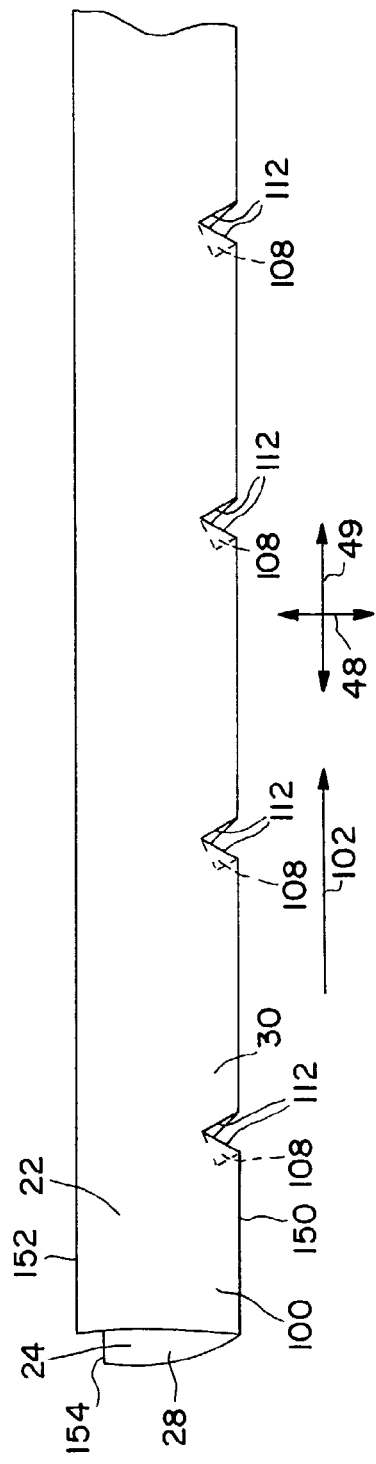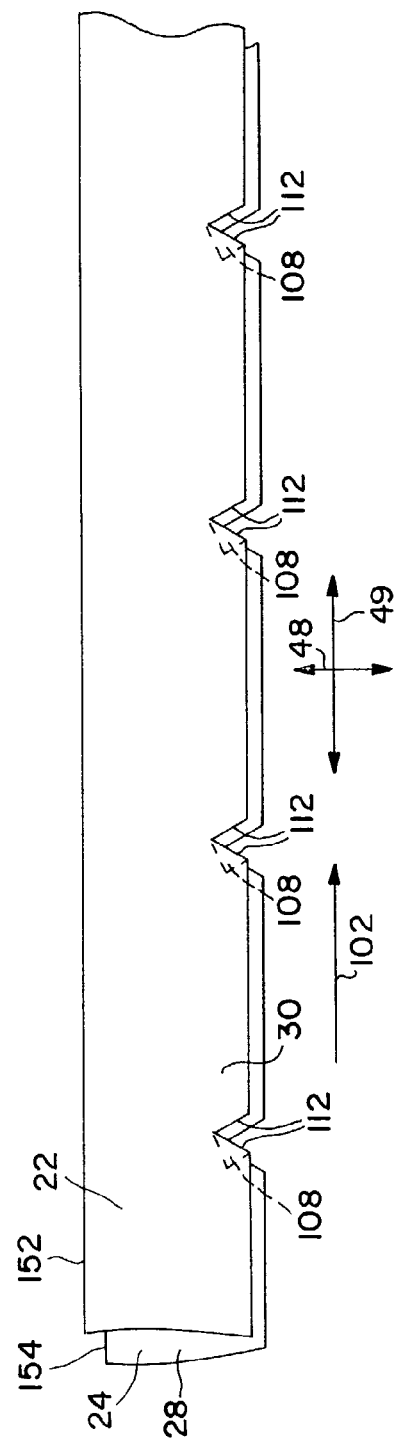

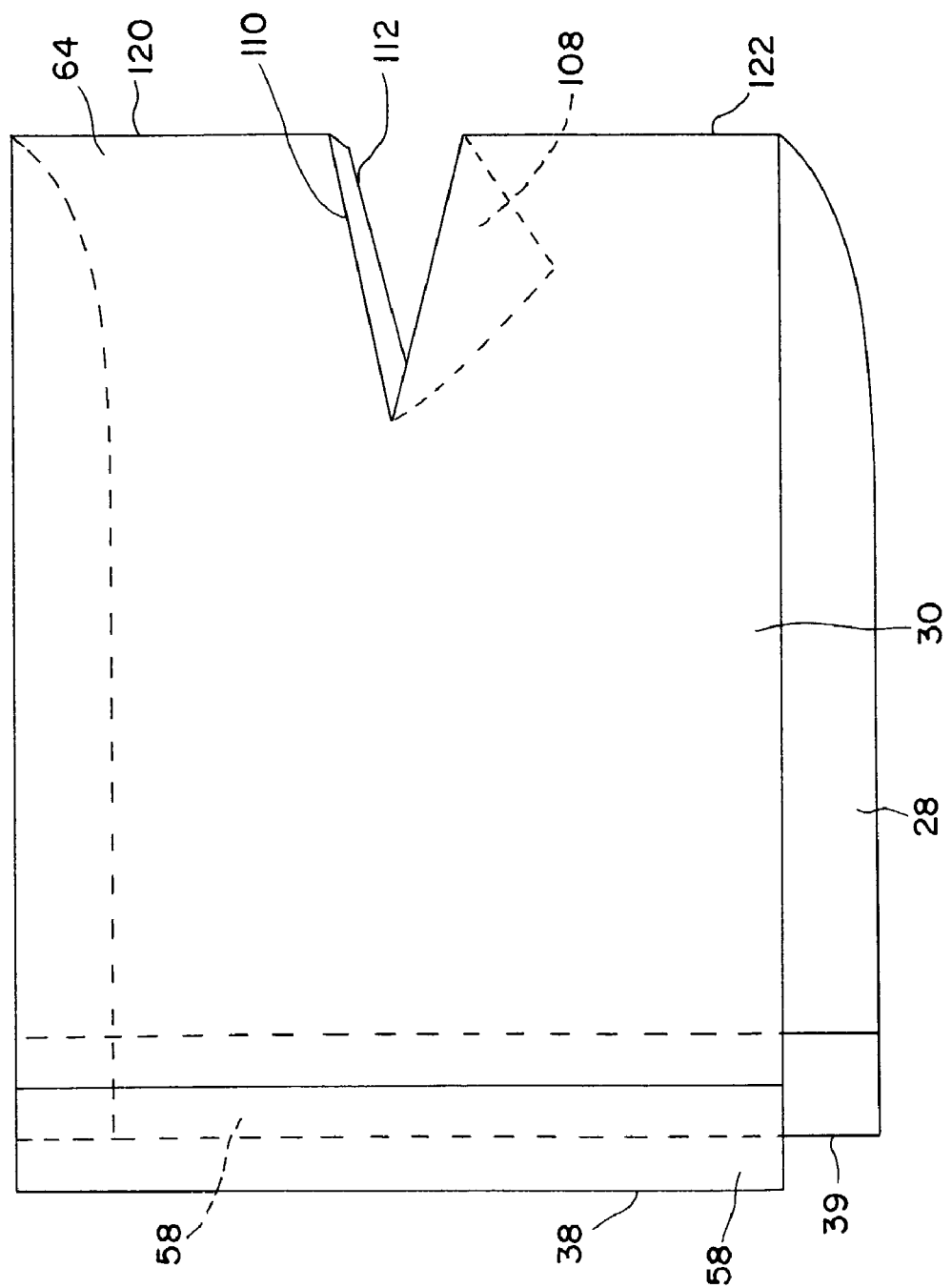

BOXER-STYLE ABSORBENT UNDERPANT AND METHOD OF MAKING SAME

BACKGROUND OF THE INVENTION

The present invention pertains to methods of making pants having side seams. More particularly, the present invention pertains to methods of making boxer shorts having side seams. The boxer shorts may be absorbent or non-absorbent.

Pant-like garments have numerous applications including disposable clothing, training pants, feminine care products, adult incontinence products, disposable swimwear, or the like. Pant-like disposable garments are typically three-dimensional products with closed sides so that the product has a unitary waist opening and two leg openings. The wearer raises and lowers the garment to apply the product. Three-dimensional, boxer shorts-like products are particularly appealing because the boxer shorts look more like conventional articles of clothes.

Many disposable pants are formed as composite structures in which several components are combined to form a product specifically suited to its intended purpose. For example, disposable pants often include one or more absorbent materials intended to absorb various bodily exudates such as urine, menstrual fluid, and/or sweat. Such products may include a liquid permeable bodyside liner and a liquid impermeable outer cover, and can include other materials and features such as elastic materials and containment structures.

However, many disposable pants can be aesthetically unappealing. Existing disposable absorbent pants can be overly bulky and can resemble disposable baby diapers. Various attempts have been made to provide disposable pants having an improved, more clothing-like appearance. However, disposable pants, particularly disposable absorbent boxer shorts, present many manufacturing challenges. In part, this is due to the high speed that is necessary to economically produce relatively low-cost disposable absorbent products. Product design is often compromised by cost and manufacturing constraints, resulting in disposable pants that lack aesthetic appeal and product function.

Thus, what is lacking and needed in the art are garment-like, aesthetically appealing boxer shorts, as well as methods of efficiently manufacturing such boxer shorts.

SUMMARY OF THE INVENTION

In response to the above-referenced unfulfilled need in the art, new pants, and methods for manufacturing such pants, have been invented. The material for the garment shell of the pant is handled as a flat web throughout assembly until seaming in order to streamline the assembly.

One aspect of the invention pertains to a method of making a pant having side seams. The method can be carried out using either machine direction assembly or cross-machine direction assembly. One embodiment of the method involves: providing a flat web and cutting at least one slit in selected areas of the flat web. In a cross-machine direction embodiment, the entire flat web is folded and the fold in the flat web is cut to provide for leg openings. The front region and back region of the flat web are joined together to form side seams and individual pants are cut from the flat web. In a machine direction embodiment, the flat web must be cut prior to the folding step. The method can include the step of attaching an absorbent structure to the flat web.

Another aspect of the present invention pertains to a pant made from a single flat web. One embodiment of the pant includes: a garment shell having a front region, a back region, a crotch region, and at least one leg opening; and at least one side-to-side crotch seam extending from the crotch region to the at least one leg opening.

The present invention relates to a wide variety of absorbent and non-absorbent pants, including training pants, swim pants, diaper pants, incontinence garments, feminine care products, health care garments, apparel for institutional, industrial and consumer use, or other garments. Disposable absorbent pants are adapted to be worn adjacent the body of a wearer to absorb and contain various exudates discharged from the body.

BRIEF DESCRIPTION OF THE DRAWINGS

These and other objects and features of this invention will be better understood from the following detailed description taken in conjunction with the drawings, wherein:

FIG. 4 is a top view of a flat web for making pants according to the present invention in the cross-machine direction;

FIG. 5 is a top view of the flat web of FIG. 4 including slits in the flat web;

FIG. 6 is a top view of the flat web of FIG. 5 showing the flaps folded back onto the flat web;

FIG. 7 is a top view of the flat web of FIG. 5 showing the flaps removed from the flat web;

FIG. 8 is a perspective view of the flat web of FIG. 6 in the folded position;

FIG. 9A is a perspective view of FIG. 8 after cutting the fold in the web;

FIG. 17 is a side perspective view of one embodiment of the method of the present invention showing an individual pant in a folded position prior to formation of the side seams.

DEFINITIONS

Figure 1A:
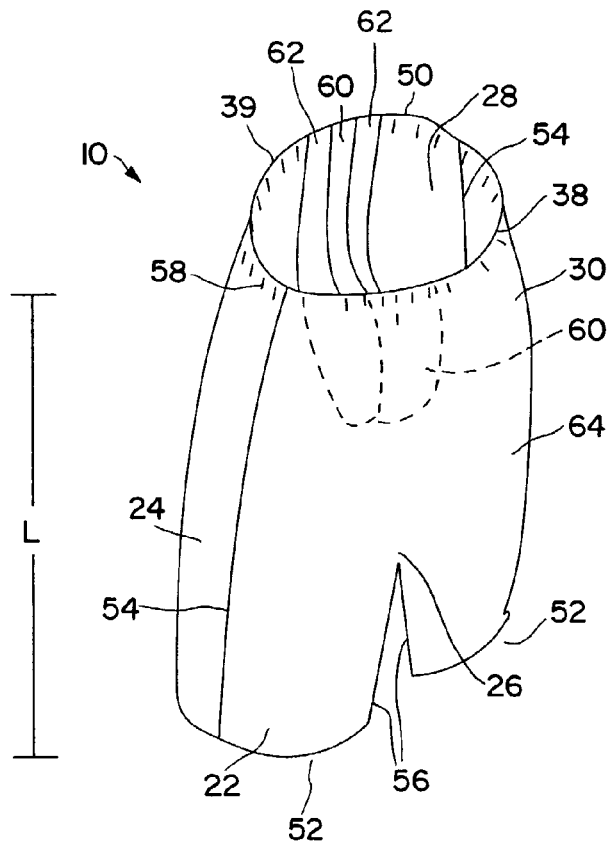
FIG. 1A is a perspective view of one embodiment of a pant according to the present invention.

Within the context of this specification, each term or phrase below will include the following meaning or meanings.

"Attached" refers to the joining, adhering, connecting, bonding, or the like, of two elements. Two elements will be considered to be attached together when they are attached directly to one another or indirectly to one another, such as when each is directly attached to intermediate elements.

"Boxer shorts" refers to a pant, trunks, briefs, and the like that have leg structures which generally extend below the crotch when worn.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all woven, knitted and nonwoven fibrous webs.

"Flat web" comprises any material used for making garments that can be provided and processed in a substantially open, unfolded state; while the web can possess ripples or areas that do not lie exactly within an overall plane of the web, all points of the web should be reasonably identifiable as constituents in either an upper or a lower surface of the web. No portions of a flat web are enclosed or fixed into a loop or tunnel-like, or three-dimensional configuration.

"Garment shell" refers to an outer cover or outer layer of a garment. In a single-ply garment, the single layer of the garment is the garment shell.

"Garment insert" refers to an inner layer of a garment. The garment insert provides a pant-like fit about a wearer's lower torso, thereby serving as a form of built-in underwear within the garment.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Machine direction" refers to the length of a fabric in the direction in which it is produced, as opposed to "cross-machine direction" which refers to the width of a fabric in a direction generally perpendicular to the machine direction.

Figure 13:
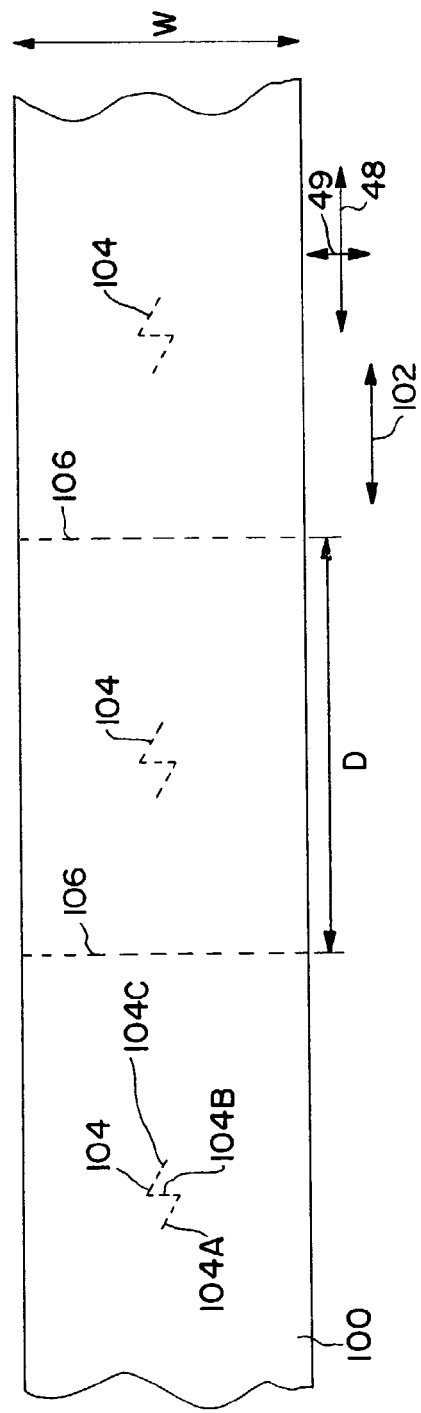
FIG. 13 a top view of the flat web of FIG. 12 including slits in the flat web

The term "machine direction assembly" refers to a process in which disposable absorbent products are manufactured in an orientation in which the products are connected end-to-end or waist-to-waist, in the longitudinal direction shown by arrow 48 in FIG. 13. A process utilizing a machine direction assembly entails products traveling through a converting machine parallel to the direction of arrow 102, as opposed to "cross-machine direction assembly" in which the products are connected side-to-side.

"Member" when used in the singular can have the dual meaning of a single element or a plurality of elements.

"Nonwoven" and "nonwoven web" and "web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Side-to-side crotch seam" refers to an inner seam of a garment.

"Stretchable" means that a material can be stretched, without breaking, by at least 50% (to 150% of its initial (unstretched) length) in at least one direction, suitably by at least 100% (to 200% of its initial length), desirably by at least 150% (to at least 250% of its initial length).

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

The term "targeted elastic regions" or "targeted elastic zones" refers to isolated, often relatively narrow regions or zones in a single composite material or layer, which have greater elastic tension than adjacent or surrounding regions or zones, as described, for example, in U.S. patent application Ser. No. 09/855,189, filed on May 14, 2001 (U.S. Publication US 2002/0002021, 03 Jan. 2002) by Raymond Jeffrey May et al. entitled "Targeted Elastic Laminate Having Zones of Different Basis Weights," and in U.S. patent application Ser. No. 09/855,188, filed on May 14, 2001 (U.S. Publication US 2002/0,009940, 24 Jan. 2002) by Raymond Jeffrey May et al. entitled "Targeted Elastic Laminate Having Zones of Different Polymer Materials," which are incorporated herein by reference.

The term "targeted elastic material" ("TEM") refers to a single elastic material or laminate having targeted elastic zones. TEMs include only materials or laminates which are made in a single manufacturing process, and which are capable of exhibiting targeted elastic properties without requiring an added elastic band or layer in the targeted elastic region. TEMs do not include materials having elasticized regions achieved through separate manufacture of an elastic band, and subsequent connection of the elastic band to the underlying material.

"Three-dimensional garment" refers to a garment that cannot be laid flat with all of its seams in one plane.

"Z-slit" refers to creating a generally Z-shaped cut, slit, or aperture in a flat web. The Z-slit may be made via one continuous slit, or multiple separate slits.

These terms may be defined with additional language in the remaining portions of the specification.

DESCRIPTION OF PREFERRED EMBODIMENTS

Figure 1B:
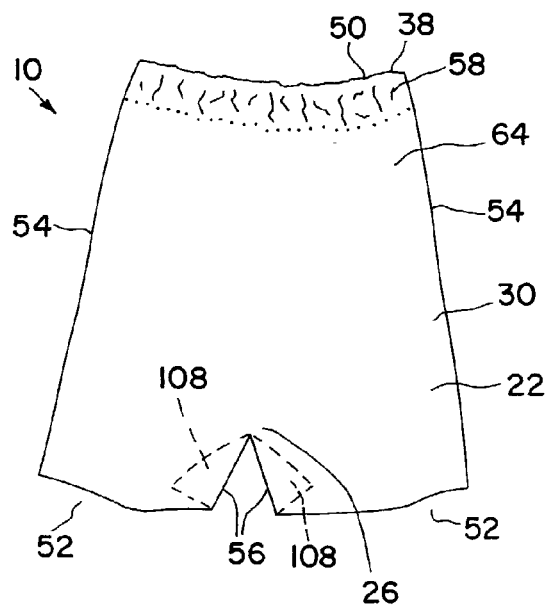
FIG. 1B is a front view of one embodiment of a pant according to the present invention.
Figure 2:
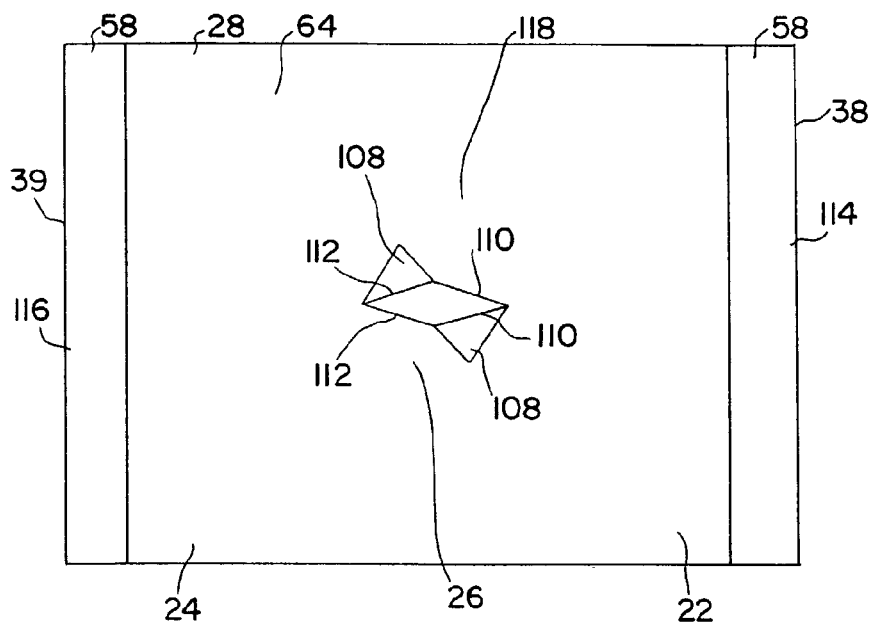
FIG. 2 a plan view of the garment shown in FIG. 1A, showing the side facing a wearer without an absorbent structure.

As representatively illustrated in FIGS. 1A, 1B and 2, an embodiment of a pant 10 of the present invention includes a garment shell 64. The garment shell 64 can include a front region 22, a back region 24, a crotch region 26, an inner surface 28 which is configured to contact the wearer, and an outer surface 30 opposite the inner surface 28 which is configured to face away from the surface of the wearer's body. The pant 10 also defines a pair of longitudinally opposed waist edges, which are designated front waist edge 38 and back waist edge 39. The front region 22 is contiguous with the front waist edge 38, and the back region 24 is contiguous with the back waist edge 39. The front region 22 includes the portion of the pant 10 which, when worn, is positioned on the front of the wearer while the back region 24 includes the portion of the pant 10 which, when worn, is positioned on the back of the wearer. The crotch region 26 of the pant 10 includes the portion of the pant which, when worn, is positioned between the legs of the wearer and covers the lower torso of the wearer. As illustrated in FIG. 1, the front and back regions 22 and 24 are joined together at side seams 54 and at side-to-side crotch seams 56 to define a three-dimensional pant configuration having a waist opening 50 and a pair of leg openings 52. In particular embodiments, the pant 10 can include an absorbent structure 60. (FIG. 1). Various embodiments of these and other features will now be described.

In particular embodiments, each of the side-to-side crotch seams 56 follows a path which begins substantially at the crotch region 26 and terminates substantially at one of the leg openings 52. In alterative embodiments, the side-to-side crotch seam 56 can follow a path which begins substantially at the crotch region 26 and terminates at a point before each leg opening 52. As another alternative, the side-to-side crotch seam 56 may be a single seam extending substantially from one leg opening 52, through the crotch region 26 and to the other leg opening 52. As is known in the art, each side-to-side crotch seam 56 (or a single side-to-side crotch seam) can be an inward or outward fin seam or lap seam (not shown).

The pant 10 also includes side seams 54 which connect the front region 22 to the back region 24 to create the pant 10. The side seams 54 can take any number of forms, including both refastenable and non-refastenable seams as is known in the art. The provision of the side seams 54 can be accomplished in the manner described in U.S. Pat. No. 5,046,272, issued Sep. 10, 1991 to Vogt et al., which is incorporated herein by reference. As is known in the art, the side seams 54 can be inward or outward fin seams or lap seams (not shown).

The pant 10 can also have a waist elastic member 58. The waist elastic member 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and elasticized or shrunk, for example with the application of heat, such that elastic constrictive forces are imparted to the substrate. In one particular embodiment, for example, the waist elastic member 58 includes a plurality of dry-spun coalesced multifilament spandex elastomeric threads sold under the trade name LYCRA® and available from E.I. du Pont de Nemours and Company, Wilmington, Del., U.S.A. In another particular embodiment, for example, the waist elastic member 58 includes Findley HX 2695-01 adhesive laminated to two facings of 0.6 osy bicomponent polypropylene/polyethylene spunbond. Alternatively, multiple strands of 310 decitex LYCRA® may be also laminated at 250% elongation between the spunbond facings in addition to the Findley adhesive. In particular embodiments, the elastic material includes a stretch-thermal laminate (STL), a neck-bonded laminated (NBL), a reversibly necked laminate, or a stretch-bonded laminate (SBL) material. Methods of making such STL, NBL and SBL materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the names of Taylor et al.; PCT Publication WO 01/88245 published on Nov. 22, 2001 in the names of Welch, et al.; all of which are incorporated herein by reference. Alternatively, the waist elastic member 58 can include other woven or nonwoven materials, such as stretchable but inelastic materials.

As another alternative, for example, in embodiments produced in the cross-machine direction discussed below, the waist elastic member 58 can be a targeted elastic zone integrated into the material of the garment shell 64. As another alternative, the waist elastic member 58 can be a "temporarily inhibited elastic." "Temporarily inhibited elastic" is described for example in U.S. Pat. No. 5,545,158 issued Aug. 13, 1996, to Jessup, U.S. Pat. No. 5,669,996 issued Sep. 23, 1997, to Jessup, and U.S. Pat. No. 5,500,063 issued Mar. 19, 1996, to Jessup, each of which is herein incorporated by reference, and references cited therein.

Figure 3:
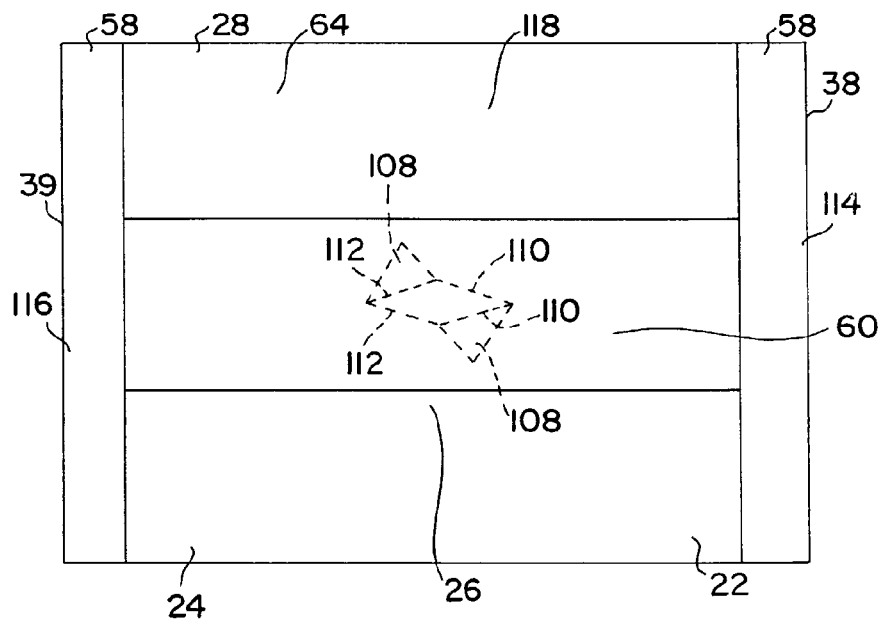
FIG. 3 a plan view of the garment shown in FIG. 1A, showing the side facing a wearer with an absorbent structure.

The pant 10 can also include an absorbent structure 60. (FIGS. 1A and 3). The absorbent structure 60 can be attached to the garment shell 64 at the front waist edge 38 and back waist edge 39, or at some point below the front waist edge 38 and back waist edge 39 on the front region 22 and back region 24. Alternatively, the absorbent structure 60 can be attached to the garment shell 64 in the crotch region 26.

The absorbent structure 60 can be any structure which is generally compressible, conformable, non-irritating to the skin, and capable of absorbing and retaining liquids and certain body wastes. The absorbent structure 60 can be manufactured in a wide variety of sizes and shapes, from a wide variety of liquid absorbent materials commonly used in the art, and may be stretchable, non-stretchable, or elastic. For example, the absorbent structure 60 can suitably include a matrix of hydrophilic fibers, such as a web of cellulosic fluff, mixed with particles of a high-absorbency material commonly known as superabsorbent material. In a particular embodiment, the absorbent structure 60 includes a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 60 to better contain and absorb body exudates. The concentration of the superabsorbent particles can also vary through the thickness of the absorbent structure 60. Alternatively, the absorbent structure 60 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent structure 60 includes a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent structure 60 in an amount of from 0 to about 90 weight percent based on total weight of the absorbent assembly. The absorbent structure 60 suitably has a density within the range of about 0.10 to about 0.35 grams per cubic centimeter. The absorbent structure 60 may or may not be wrapped or encompassed by a suitable tissue wrap that may help maintain the integrity and/or shape of the absorbent assembly.

The absorbent structure 60 can also incorporate other materials that are designed primarily to receive, temporarily store, and/or transport liquid along the mutually facing surface with absorbent structure 60, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C. U.S.A.

In particular embodiments, the absorbent structure 60 is thin to provide a slim, comfortable, non-bulky pant 10. Any suitable thin absorbent structure may be used, such as for example, the thin absorbent described in WO 02/49565, published Jun. 27, 2002, by Sawyer et al., which is incorporated herein by reference.

The absorbent structure 60 can include a pair of containment flaps 62 (FIG. 1A) which are configured to provide a barrier to the transverse flow of body exudates. A flap elastic member (not shown) can be operatively joined with each containment flap 62 in any suitable manner as is well known in the art. The elasticized containment flaps 62 define an unattached edge which assumes an upright, generally perpendicular configuration in at least the crotch region 26 of the pant 10 to form a seal against the wearer's body. Suitable constructions and arrangements for the containment flaps 62 are generally well known to those skilled in the art and are described in U.S. Pat. No. 4,704,116 issued Nov. 3, 1987 to Enloe, which is incorporated herein by reference.

Alternatively, a pant-like garment insert could be used for the absorbent structure 60. For example, the pant-like garment insert suitably includes a body side liner, an outer cover, and an absorbent assembly between the body side liner and the outer cover, and side panels. An example of a suitable insert is a training pant, such as HUGGIES® PULL-UPS® Disposable Training Pants, manufactured by Kimberly-Clark Corporation, Neenah, Wis., U.S.A.

As another alternative, a pad-type absorbent could be used for the absorbent structure. The pad-type absorbent can be attached in the crotch-region 26 of the pant 10. An example of a suitable pad-type absorbent is a feminine care pad such as KOTEX® Feminine Napkins, KOTEX® LIGHTDAYS® disposable panty liners, or an incontinence absorbent pad such as POISE® Feminine Guards and Pads or DEPEND® Guards for Men, all manufactured by Kimberly-Clark Corporation, Neenah, Wis., U.S.A.

The garment shell 64 is desirably constructed of materials which are comfortable against the skin and non-irritating. It is contemplated that the garment shell 64 can be either disposable or durable, i.e., launderable, in the embodiments without an absorbent structure, and disposable in the embodiments with an absorbent structure. Both nonwoven and woven materials are contemplated for the garment shell 64. For example, the garment shell 64 for pant 10 can be selected from a wide variety of materials, including elastic, stretchable, or nonstretchable materials. The garment shell 64 can be a single layer of material or a multi-layered laminate structure. A suitable material includes a spunbond polypropylene nonwoven web having a basis weight preferably greater than 20 gsm (grams per square meter). Another example of a suitable material is a neck-stretched 42 gsm spunbond polypropylene nonwoven web. The garment shell 64 may also be made of those materials of which the absorbent structure 60 is made. It is desired that the garment shell 64 provide a relatively cloth-like texture to the wearer.

In particular embodiments, the garment shell 64 includes a stretchable material, for example, the previously described stretch-bonded laminate material, the previously described LYCRA® material, stretchable nylon, and the like. In addition, in particular embodiments, to provide better fit through the crotch region 26, the garment shell 64 can be elastomeric.

Figure 12:
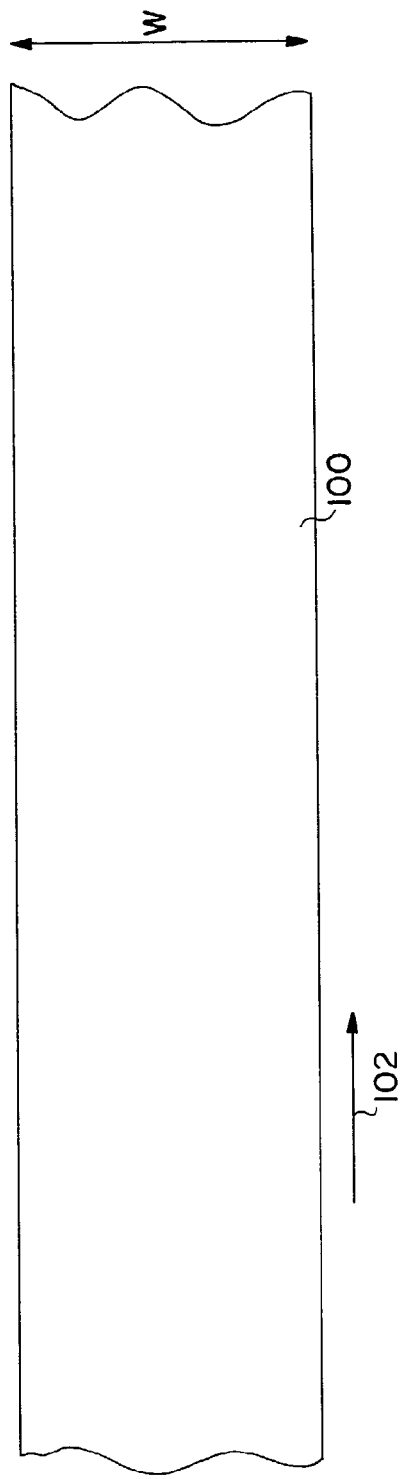
FIG. 12 is a top view of a flat web for making pants according to the present invention in the machine direction.

The present invention also includes various methods for making pants having side seams from a flat web, as shall now be explained and illustrated. Referring to FIGS. 4 and 12, a single flat web 100 is provided moving in the direction represented by arrow 102. Alternatively, two webs that are joined at their edges to form a double-width piece (not shown) can be used for the flat web 100. The flat web 100 can be composed of any material previously described for the garment shell 64.

The method of the present invention can be carried out using machine direction assembly so that arrow 102 can correspond to the longitudinal direction as shown by arrow 48 (FIG. 13) with the products connected end to end or waist to waist. Alternatively, the method of the present invention can be carried out using cross-machine direction assembly so that arrow 102 can correspond to the transverse direction as shown by arrow 49 (FIG. 5) with the products connected side-to-side.

In the cross-machine direction process (FIGS. 5–11), a slit 104 is cut in the flat web 100 in selected areas between cut lines 106. Cut lines 106 represent the areas where the flat web 100 will eventually be cut to form individual pants 10. The width W of flat web 100 in the cross-machine direction (FIG. 5) must be about twice the desired length L of the pant 10 (FIG. 1). In particular embodiments, each slit 104 is provided substantially in the center of the selected areas between the cut lines 106. Cutting the slit 104 can be accomplished, for example, using a rotary knife (not shown). Alternatively, any other suitable slitting method known in the art can be used. Following cutting the slits 104, any trim can be removed if necessary by vacuum (not shown).

In particular embodiments, slits 104 are z-slits as shown in FIG. 5. It is also contemplated that the slit 104 can include any shape or pattern as long as the shape of the slit 104 creates two triangular flaps. Each z-slit 104 includes three lines, an upper line 104A, a middle line 104B and a lower line 104C. Middle line 104B of the slit 104 is desirably located in the center of the flat web 100 in the cross-machine direction and can range in length from 5% to 30% of the width (W) of the flat web 100. Upper line 104A and lower line 104C can range in length from 5% to 30% of the width (W) of the flat web 100. The length of lines 104A and 104C correspond to the length of each side-to-side crotch seam 56.

Referring to FIG. 6, cutting the slit 104 defines two flaps 108 which can be lifted up from the flat web 100 and folded back upon the flat web 100 by mechanical, pneumatic or vacuum means known in the art. The flaps 108 can be attached to the flat web 100 by ultrasonic, thermal or adhesive bonding, sewing or by any other appropriate method known in the art. Cutting the slit 104 also defines two first seam edges 110 and two second seam edges 112. The flaps 108 define an upper facing surface as shown in FIG. 6. Folding the flaps 108 back and bonding them to the flat web 100 minimizes any waste in the manufacturing process that can be associated with removing and discarding portions of the flat web 100. However, it is also contemplated that the flaps 108 can be removed by any suitable method known in the art to define diamond shaped cut-outs. (FIG. 7). Removing the flaps 108 also defines two first seam edges 110 and two second seam edges 112. (FIG. 7) Alternatively, a diamond (or any other suitable) shape piece can be removed from the flat web 100 to define the first and second seam edges 110 and 112.

Figure 10:
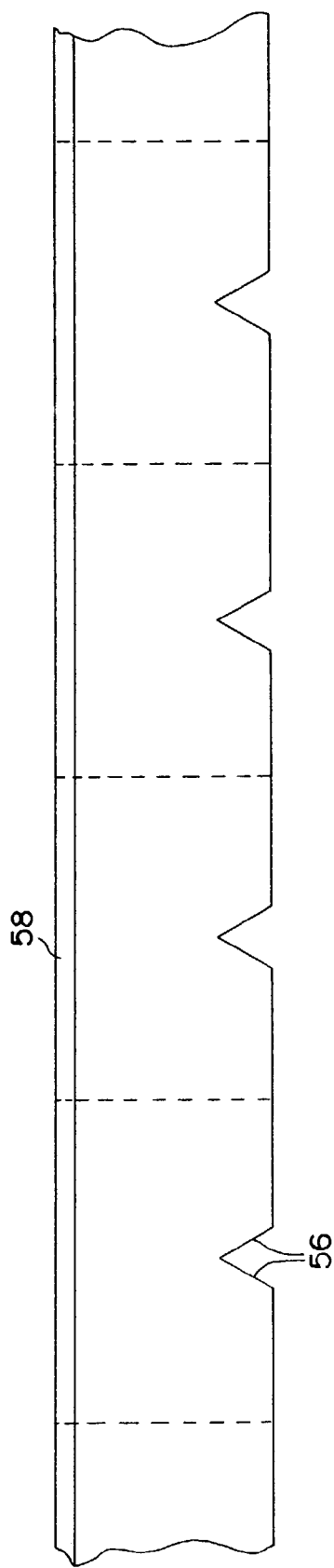
FIG. 10 is a front view of FIG. 9B and further including a waist elastic member.

FIGS. 6 and 10 also show waist elastic member 58 applied to the flat web 100 and on the folded web prior to formation of the side seams. The waist elastics 58 can be applied by any method known in the art at any stage in the manufacturing of the pant 10.

Referring to FIG. 8, the flat web 100 can now be folded in the cross-machine direction by methods known in the art. Folding the flat web 100 defines a fold 150 in the flat web 100 running along the length of the flat web 100 in the direction of arrow 102. Folding the flat web 100 also defines a first waist edge 152 and a second waist edge 154 of the flat web 100, corresponding to the front waist edge 38 and the back waist edge 39 (FIG. 1) of the finished pant 10. The flat web 100 also defines an inner surface 28 and an outer surface 30, corresponding to the inner and outer surfaces 28 and 30 of the pant (FIG. 1), and a front region 22 and a back region 24 corresponding to the front and back regions 22 and 24 of the pant 10 (FIG. 1). It is also contemplated that the pants 10 can be made upside-down, i.e., with the fold 150 facing upwardly (not shown).

Referring to FIG. 9A, in order to provide the leg openings 52 for the pant 10, the fold 150 is cut by, for example, a rotary cutter (not shown). Alternatively, a water cutter jet (not shown) or an ultrasonic cutter (not shown) may be used to cut the fold 150. Alternatively, any other means known in the art may be used to cut the fold 150.

Figure 9B:
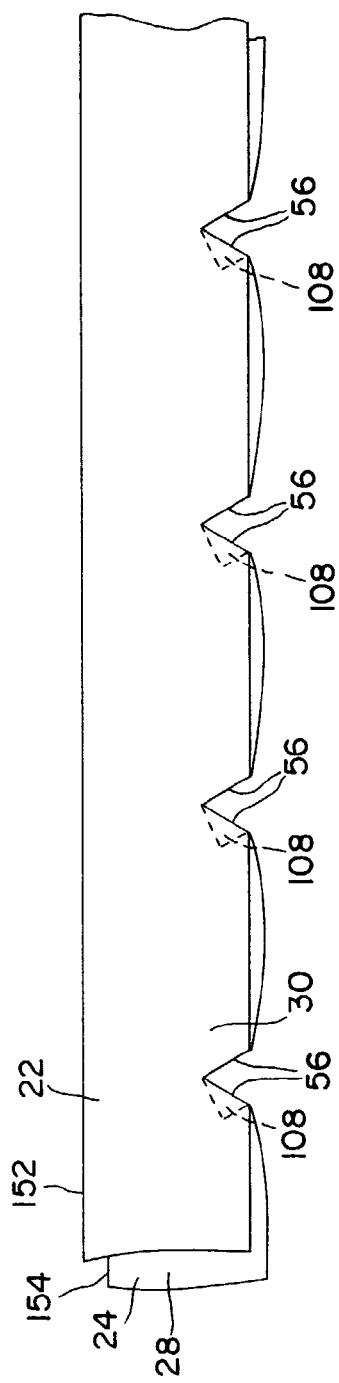
FIG. 9B is a perspective view of FIG. 9A after formation of the side-to-side crotch seams.

In particular embodiments, no z-slit is made in the flat web 100 and the garment shell 64 of the pant 10 can be in a skirt format (not shown). Referring to FIG. 9B, in particular embodiments, the side-to-side crotch seams 56 connecting the front region 22 of the flat web 100 to the back region 24 of the web 100 can be formed by conventional bonding methods by, for example, ultrasonic, thermal or adhesive bonding. In particular embodiments, adhesive can be added to the upper facing surface of the flaps 108 so that after the flat web 100 is folded, the inner surface of the flat web 100 will attach to the upper facing surface of the flaps. This will improve the garment-like appearance of the eventual crotch seams 56. Once folded, the upper facing surface of flap 108 integral with the back region 24 will attach to the inner surface 28 of the front region 22 to form one crotch seam 56. Likewise, the upper facing surface of flap 108 integral with the front region 22 will attach to the inner surface 28 of the back region 24 to form the other crotch seam 56.

As previously mentioned, in particular embodiments, the side-to-side crotch seam 56 may be a single seam extending from one leg opening 52 through the crotch region 26 to the other leg opening 52. In this embodiment, the single side-to-side crotch seam may be formed using, for example, an ultrasonic plunge bonder (not shown), or a rotary ultrasonic bonder (not shown), or by adhesive bonding.

Figure 11:
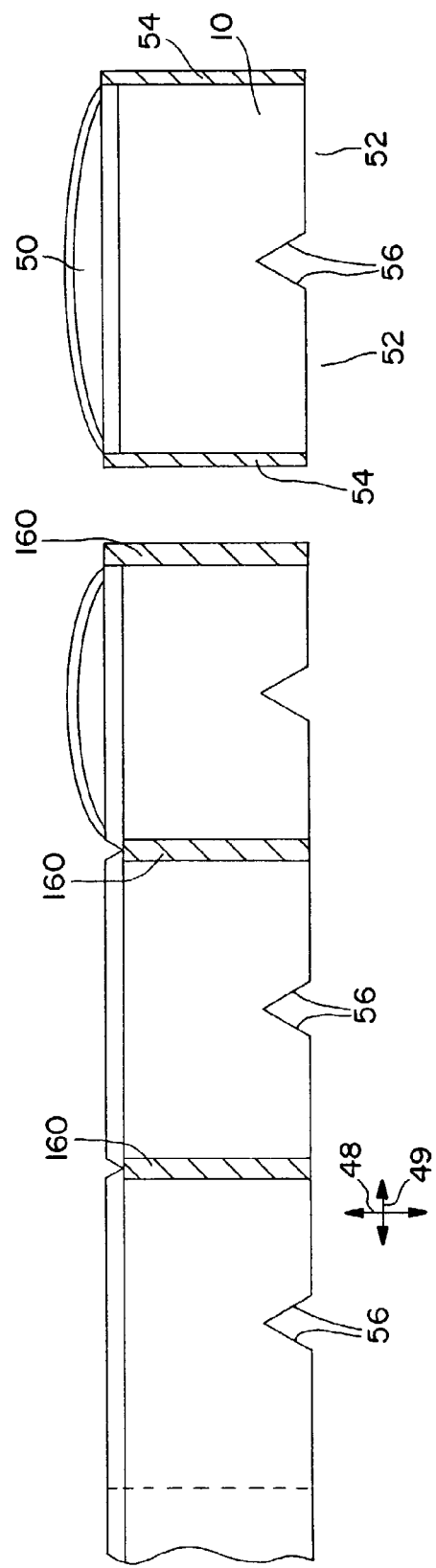
FIG. 11 is a schematic view of one embodiment of the method of the present invention showing an individual pant cut from the web.

The front and back regions 22 and 24 of the flat web 100 are bonded together at a plurality of locations in the longitudinal direction 48 to define a plurality of web side seams 160, each web side seam 160 positioned longitudinally (FIG. 11). The web side seams 160 correspond to the side seams 54 in the pant 10 (FIG. 1). It is also contemplated that the step of forming the side-to-side crotch seams 56 can be performed prior to the step of forming the side seams. The web is cut by any suitable method known in the art into a plurality of disposable pants 10, each disposable pant having a waist opening 50, two leg openings 52, side seams 54, and a side-to-side crotch seam 56. The cutting can be accomplished by rotary or plunge-type die cutting, ultrasonic cutting, laser, or by any other method known in the art.

Referring to FIGS. 1 and 3, in particular embodiments, in the cross-machine direction process, an absorbent structure 60 is included in the pant 10. The absorbent structure 60 can be introduced into the pant 10 by being attached to the flat web 100 in any suitable manner known in the art at any point in the manufacturing process. In particular embodiments, the absorbent structure 60 can be placed on top of the flaps 108 on the inner surface 28 of the flat web 100. The absorbent structure 60 can be attached to the flat web 100 at the first waist edge 152 and second waist edge 154, or at some point below the first waist edge 152 and second waist 154 on the front region 22 and back region 24. In the cross-machine direction process, it is contemplated that the absorbent structure 60 can be attached to the flat web 100 at any point prior to the folding step, and before formation of the side seams 54. It is also contemplated that the absorbent structure 60 can be attached to the flat web 100 after the folding of the flat web 100, but prior to formation of the side seams. In addition, it is also contemplated that the absorbent structure 60 can be folded first and attached to the flat web 100. The attachment of the absorbent structure 60 can be accomplished by ultrasonic, thermal or adhesive bonding, or any other suitable method known in the art. Also, although it is contemplated to attach the absorbent structure 60 prior to folding and cutting off individual pants 10, it is also contemplated that the absorbent structure 60 can be attached after folding and cutting the web into separate pieces (not shown).

In the machine direction process (FIGS. 12–17), a flat web 100 with width W (FIG. 12) is provided in the direction of arrow 102. A slit 104 is cut in the flat web 100 in selected areas between cut lines 106. (FIG. 13) Cut lines 106 represent the areas where the flat web 100 will eventually be cut to form individual garment shells 64. The distance D (FIG. 13) between each cut line 106 must be about twice the desired length L of the pant 10 (FIG. 1). In particular embodiments, each slit 104 is provided substantially in the center of the selected areas between the cut lines 106. Cutting the slit 104 can be accomplished, for example, using a rotary knife (not shown). Alternatively, any other suitable slitting method known in the art can be used. This step of cutting a slit 104 can, as explained and illustrated here, be performed before the step of cutting the flat web 100 along cut lines 106 to form individual garment shells 64. Alternatively, it is also contemplated that the step of cutting the slits 104 can be performed after the step of cutting the flat web 100 into individual garment shells 64. Following cutting the slits 104, any trim can be removed if necessary by vacuum (not shown).

In particular embodiments, slits 104 are z-slits as shown in FIG. 13. It is also contemplated that the slit 104 can include any shape or pattern as long as the shape of the slit 104 creates two triangular flaps. Each z-slit 104 includes three lines, an upper line 104A, a middle line 104B and a lower line 104C. Middle line 104B of the slit 104 is desirably located in the center of the flat web 100 in the cross-machine direction and can range in length from 5% to 30% of the width (W) of the flat web 100. Upper line 104A and lower line 104 C can range in length from 5% to 30% of the width (W) of the flat web 100. The length of lines 104A and 104C correspond to the length of each side-to-side crotch seam 56.

Figure 14:
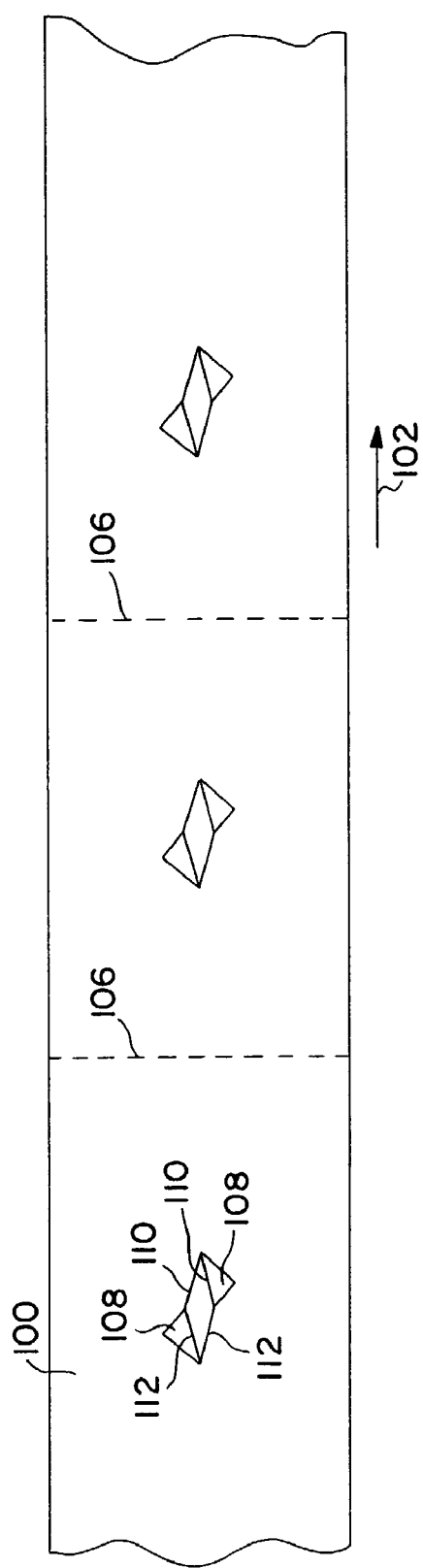
FIG. 14 is a top view of the flat web of FIG. 13 showing the flaps folded back onto the flat web.
Figure 15:
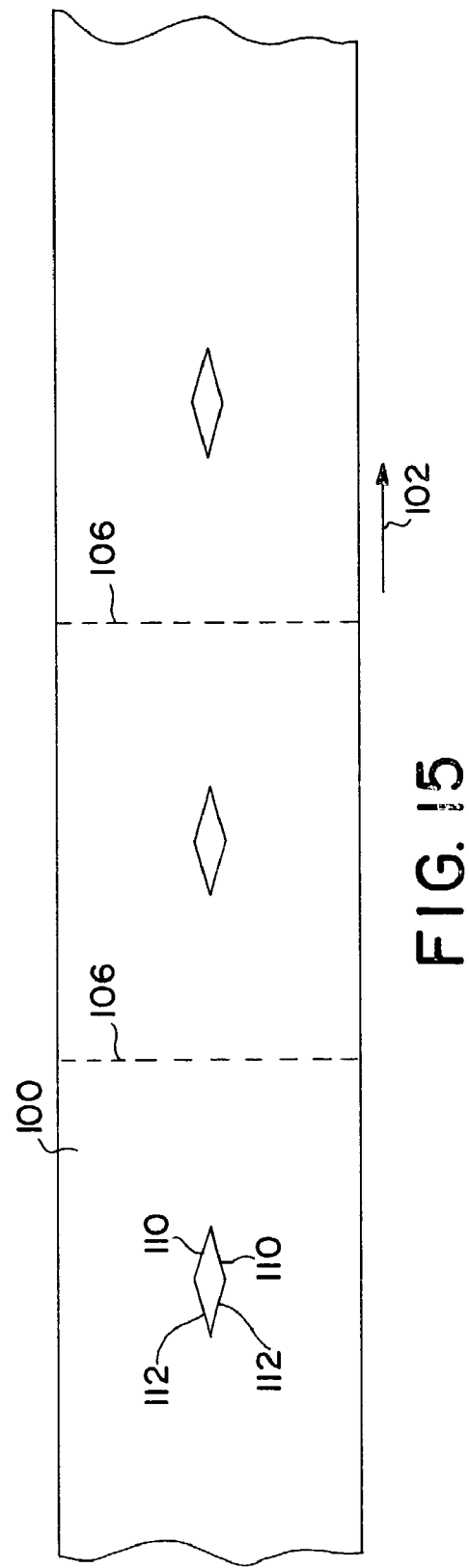
FIG. 15 is a top view of the flat web of FIG. 13 showing the flaps removed from the flat web.

Referring to FIG. 14, cutting the slit 104 defines two flaps 108 which can be lifted up from the flat web 100 and folded back upon the flat web 100 by mechanical, pneumatic, or vacuum means known in the art. The flaps 108 can be attached to the flat web 100 by ultrasonic, thermal or adhesive bonding, or by any other appropriate method known in the art. Cutting the slit 104 also defines two first seam edges 110 and two second seam edges 112. The flaps 108 define an upper facing surface as shown in FIG. 14. Folding the flaps 108 back and bonding them to the flat web 100 minimizes any waste in the manufacturing process that can be associated with removing and discarding portions of the flat web 100. However, it is also contemplated that the flaps 108 can be removed by any suitable method known in the art (FIG. 15). Removing the flaps 108 also defines two first seam edges 110 and two second seam edges 112. Alternatively, a diamond (or any other suitable) shape piece can be removed from the flat web 100 to define the first and second seam edges 110 and 112.

Figure 16:
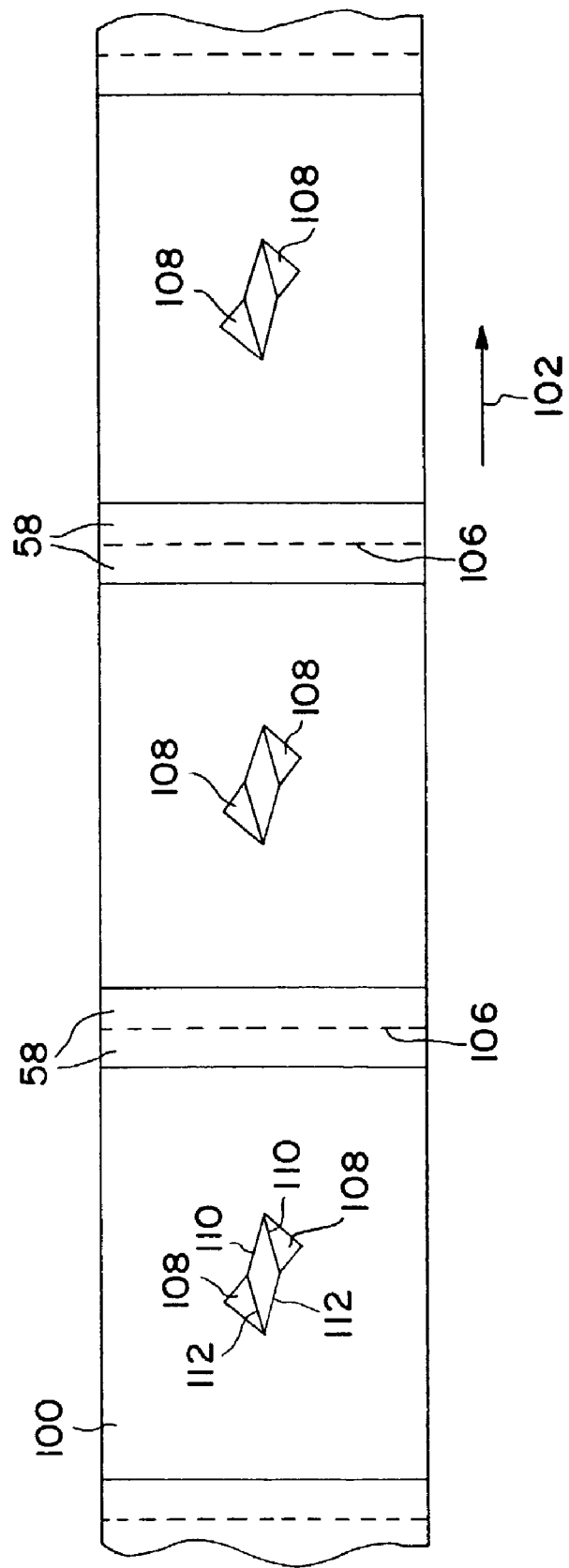
FIG. 16 is a top view of FIG. 14 and further including a waist elastic member.

FIG. 16 also shows waist elastics 58 applied to the flat web 100. The waist elastics 58 can be applied by any method known in the art at any stage in the manufacturing of the pant 10.

The flat web 100 at this point includes a continuous series of garment shells. In order to separate one garment shell from the continuous series of garment shells, the flat web 100 is cut along cut line 106 into separate pieces to define individual garment shells 64. (FIG. 2) The cutting can be accomplished, for example, using a cutting roll (not shown). Alternatively, any other suitable cutting method known in the art can be used.

Referring to FIG. 2, as previously mentioned, the flat web 100 has now been cut into separate pieces to form a garment shell 64 prior to folding and formation of the side seams 54. Each piece defines a leading edge 114, a trailing edge 116 and a center region 118 between the leading edge 114 and the trailing edge 116. As shown and as previously mentioned with respect to FIG. 1, the garment shell 64 can include a front region 22, a back region 24, a crotch region 26, an inner surface 28, and an outer surface 30 (not shown), front waist edge 38 (which can correspond to the leading edge 114 or the trailing edge 116), back waist edge 39 (which can correspond to, the leading edge 114 or the trailing edge 116), and waist elastic member 58. The bonding together of first and second seam edges 110 and 112, as previously described, will form the side-to-side crotch seams 56. It is also contemplated that the garment shell 64 can be made upside-down, i.e., with the inner surface 28 facing downwardly (not shown) with the flaps 108 facing downwardly.

The garment shell 64 can be folded by any conventional method known in the art to form the folded garment shell 64, as shown in FIG. 17. Folding the garment shell 64 defines a first fold 120 and a second fold 122. In order to provide the leg openings 52, the first and second folds 120, 122 are cut by, for example, a rotary cutter. Alternatively, a water cutter jet (not shown), or an ultrasonic cutter (not shown) may be used to cut the folds 120, 122 to provide the leg openings 52. Alternatively, any other means known in the art may be used to cut the folds 120, 122. The side seams 54 may be formed by any means known in the art to form the pant 10. It is also contemplated that the step of forming the side seams 54 may be performed prior to the step of cutting the folds 120, 122.

In particular embodiments, no z-slit is made in the flat web 100 and the garment shell 64 can be in a skirt format (not shown). In particular embodiments, the side-to-side crotch seams 56 can be formed by conventional bonding methods by, for example, ultrasonic, thermal or adhesive bonding. In particular embodiments, adhesive can be added to the upper facing surface of the flaps so that after the flat web 100 is folded, the inner surface of the flat web will attach to the upper facing surface of the flaps. This will improve the garment-like appearance of the eventual crotch seams 56. Once folded, the upper facing surface of flap 108 integral with the back region 24 will attach to the inner surface 28 of the front region 22 to form one crotch seam 56. Likewise, the upper facing surface of flap 108 integral with the front region 22 will attach to the inner surface 28 of the back region 24 to form the other crotch seam 56.

As previously mentioned, in particular embodiments, the side-to-side crotch seam may be a single seam extending from one leg opening 52 through the crotch region 26 to the other leg opening 52. In this embodiment, the single side-to-side crotch seam may be formed using, for example, an ultrasonic plunge bonder (not shown), or a rotary ultrasonic bonder, or by adhesive bonding.

In either the cross-machine direction process or the machine direction process, it is contemplated that the crotch seams 56 can be made either before or after the leg openings 52 are provided.

Referring to FIGS. 1A and 3, in particular embodiments, in the machine direction process, an absorbent structure 60 is included in the pant 10. The absorbent structure 60 can be introduced into the pant 10 in any suitable manner known in the art. In particular embodiments, the absorbent structure 60 can be placed on top of the flaps 108 on the inner surface 28 of the garment shell 64. The absorbent structure 60 can be attached to the garment shell 64 at the front waist edge 38 and back waist edge 39 (FIGS. 1A and 3), or at some point below the front waist edge 38 and back waist edge 39 on the front region 22 and back region 24. In the machine direction process, it is contemplated that the absorbent structure 60 can be attached to the garment shell 64 either before or after cutting of the flat web to form the garment shells 64. In addition, it is also contemplated that, as in the cross-machine direction process, the absorbent structure 60 can be folded first and attached to the garment shell 64. The attachment can be accomplished by ultrasonic, thermal or adhesive bonding, or any other suitable method known in the art. Attachment to the front and back regions 22 and 24 provides for a loose fit in the crotch region 26. In particular embodiments, the absorbent structure 60 is stretchable in order to provide the desired close to the body fit for the absorbent structure 60 while the garment shell 64 hangs loosely.

In either the cross-machine direction process or the machine direction process, in particular embodiments, vacuum (not shown) can be applied under the flat web 100 in the region to correspond to the crotch region 26 to provide a three dimensional pattern. The application of the vacuum would provide additional depth for the garment shell 64 in the crotch region 26.

As previously mentioned, it is contemplated that the pant 10 can be manufactured either with, or without and absorbent structure 60. In those embodiments of the pant 10 manufactured without an absorbent structure 60, it is contemplated that the pant 10 can be launderable and packaged together with a separate absorbent structure, such as, for example, a training pant. Alternatively, an absorbent structure could be purchased separately, such as previously mentioned, a training pant, such as Huggies® Pull-Ups® Disposable Training Pants.

The various components of the pant can be connected together by any means known to those skilled in the art such as, for example, adhesive, thermal and/or ultrasonic bonds, and also sewing and other methods used in durable garment manufacturing. Desirably, most of the components are connected using ultrasonic bonding for improved manufacturing efficiency and reduced raw material costs. For example, in particular embodiments, the side-to-side crotch seams 56 and the side seams 54 are made using ultrasonic bonding. Certain garment manufacturing equipment which is readily known and understood in the art, including frames and mounting structures, ultrasonic and adhesive bonding devices, transport conveyors, transfer rolls, guide rolls, tension rolls, and the like, have not been shown in the Figures.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

I claim:

1. A method of making a pant having side seams, comprising:
    providing a flat web;
    cutting at least one slit in selected areas of the flat web, the at least one slit creating at least one flap in the flat web;
    folding the flat web to define at least one fold, a first waist edge, a second waist edge, a front region and a back region;
    cutting the at least one fold to define at least one leg opening;
    bonding the front region and the back region together to define at least two side seams; and
    attaching the front region to the back region to form at least one side-to-side crotch seam.

2. The method of claim 1, wherein the at least one slit comprises a z-slit.

3. The method of claim 1, further comprising the step of attaching at least one waist elastic member to the flat web.

4. The method of claim 1, further comprising the step of folding the at least one flap.

5. The method of claim 4, further comprising the step of attaching the at least one flap to the flat web.

6. The method of claim 1, further comprising the step of removing the at least one flap from the flat web.

7. The method of claim 1, wherein the at least one flap comprises a triangular flap.

8. The method of claim 1, wherein the flat web comprises a continuous series of garment shells, further comprising the step of cutting the flat web to separate one garment shell from the continuous series of garment shells.

9. The method of claim 1, further comprising the step of attaching at least one absorbent structure to the flat web.

10. A method of making a pant having side seams, comprising:

providing a flat web;

cutting at least one slit in selected areas of the flat web, the at least one slit creating at least one flap in the flat web;

cutting the flat web into separate pieces, each separate piece defining a leading edge, a trailing edge, and a center region;

folding each separate piece to define at least one fold separating a front region from a back region;

cutting the at least one fold to define at least one leg opening;

bonding the front region to the back region to form at least two side seams; and attaching the front region to the back region to form at least one side-to-side crotch seam.

11. The method of claim 10, wherein the slit comprises a z-slit.

12. The method of claim 10, further comprising the step of attaching at least one waist elastic member to the flat web.

13. The method of claim 10, further comprising the step of folding the at least one flap.

14. The method of claim 13, further comprising the step of attaching the at least one flap to the flat web.

15. The method of claim 10, further comprising the step of removing the at least one flap from the flat web.

16. The method of claim 10, wherein the at least one flap comprises a triangular flap.

17. The method of claim 10, further comprising the step of attaching at least one absorbent structure to the flat web.

* * * * *